(12) United States Patent
Glensbjerg

(10) Patent No.: US 8,906,697 B2
(45) Date of Patent: Dec. 9, 2014

(54) METHOD FOR THE ASSESSMENT OF PARTICLES AND A SYSTEM AND DEVICE FOR USE IN THE METHOD

(75) Inventor: Martin Glensbjerg, Brønshøj (DK)

(73) Assignee: ChemoMetec A/S, Allerød (DK)

(*) Notice: Subject to any disclaimer, the term of this patent is extended or adjusted under 35 U.S.C. 154(b) by 1452 days.

(21) Appl. No.: 11/296,662

(22) Filed: Jun. 23, 2005

(65) Prior Publication Data
US 2007/0207551 A1 Sep. 6, 2007

Related U.S. Application Data

(63) Continuation of application No. 09/830,557, filed as application No. PCT/DK99/00605 on Nov. 5, 1999, now abandoned.

(30) Foreign Application Priority Data

Nov. 5, 1998 (DK) .................................. 1998 01433
Nov. 11, 1998 (DK) .................................. 1998 01469

(51) Int. Cl.

| | | |
|---|---|---|
| G01N 21/76 | (2006.01) |
| G01N 35/08 | (2006.01) |
| G01N 1/18 | (2006.01) |
| G01N 33/04 | (2006.01) |
| G01N 21/64 | (2006.01) |
| G01N 15/14 | (2006.01) |
| B01L 3/00 | (2006.01) |

(52) U.S. Cl.
CPC .......... *G01N 15/147* (2013.01); *G01N 15/1434* (2013.01); *B01L 3/502715* (2013.01); *G01N 15/1475* (2013.01); *B01L 2300/021* (2013.01)
USPC ............... 436/172; 436/52; 436/177; 422/74; 422/82.05; 422/82.08

(58) Field of Classification Search
CPC .................... B01L 3/502715; B01L 2300/021; G01N 15/1434; G01N 15/1475
USPC ........ 422/81, 82.05–82.11, 101–103; 436/52, 436/164, 172, 177
See application file for complete search history.

(56) References Cited

U.S. PATENT DOCUMENTS

| | | | |
|---|---|---|---|
| 4,088,448 A | 5/1978 | Lilja et al. ........................ | 23/259 |
| 4,330,206 A | 5/1982 | Gausmann et al. ........... | 356/246 |

(Continued)

FOREIGN PATENT DOCUMENTS

| | | |
|---|---|---|
| EP | 0 392 851 | 10/1990 |
| EP | 0 679 889 | 11/1995 |

(Continued)

*Primary Examiner* — Bao Thuy L Nguyen
*Assistant Examiner* — Gary E Hollinden
(74) *Attorney, Agent, or Firm* — Gifford, Krass, Sprinkle, Anderson & Citkowski, P.C.

(57) ABSTRACT

A method and a device for the assessment of at least one parameter of particles in a liquid analyte material are disclosed. The method comprises providing a device having a sample compartment with an exposing domain, an inlet through which a volume of a liquid sample representing the analyte material can been introduced, and a flow system comprising at least a channel allowing at least a portion of the volume of the liquid sample to flow within the device. The volume of the liquid sample passes into the exposing domain of the sample compartment, which can quantitatively detect spatial image data and process the detected image electromagnetic signals from the sample in the exposing domain of the device. A spatial image representation of the exposing domain, and processing the detected image presentation obtaining the assessment of the at least one parameter is generated in the device.

18 Claims, 6 Drawing Sheets

(56) References Cited

U.S. PATENT DOCUMENTS

| | | | |
|---|---|---|---|
| 4,338,024 A | 7/1982 | Bolz et al. ................... 356/23 |
| 4,560,269 A | 12/1985 | Baldszun et al. ............. 356/246 |
| 4,874,691 A * | 10/1989 | Chandler ................... 435/7.92 |
| 5,128,104 A | 7/1992 | Murphy et al. ............... 422/102 |
| 5,208,147 A | 5/1993 | Kagenow et al. .............. 435/14 |
| 5,221,605 A * | 6/1993 | Bard et al. ................... 435/4 |
| 5,300,779 A | 4/1994 | Hillman et al. |
| 5,371,020 A | 12/1994 | Frischauf ................... 436/165 |
| 5,457,526 A | 10/1995 | Kosaka ....................... 356/72 |
| 5,469,251 A | 11/1995 | Kosaka et al. ................. 356/73 |
| 5,517,870 A | 5/1996 | Kurimura et al. ............. 73/865.5 |
| 5,571,479 A | 11/1996 | Koch ........................ 422/102 |
| 5,627,041 A | 5/1997 | Shartle |
| 5,674,457 A | 10/1997 | Williamsson et al. .......... 422/102 |
| 5,681,529 A * | 10/1997 | Taguchi et al. ................ 422/61 |
| 5,726,026 A * | 3/1998 | Wilding et al. ............... 435/7.21 |
| 5,741,412 A | 4/1998 | Dovichi et al. ............... 204/602 |
| 5,755,942 A * | 5/1998 | Zanzucchi et al. .............. 506/32 |
| 5,800,784 A | 9/1998 | Horn ......................... 422/101 |
| 5,863,801 A * | 1/1999 | Southgate et al. ............. 436/63 |
| 5,912,134 A | 6/1999 | Shartle |
| 5,918,273 A | 6/1999 | Horn ........................ 73/61.55 |
| 5,935,864 A | 8/1999 | Schramm et al. ............. 436/174 |
| 5,939,326 A | 8/1999 | Chupp et al. ................. 436/43 |
| 5,962,215 A | 10/1999 | Douglas et al. ................. 435/4 |
| 6,143,247 A * | 11/2000 | Sheppard et al. ............... 422/63 |
| 6,479,299 B1 * | 11/2002 | Parce et al. ................... 436/514 |
| 2001/0055812 A1 * | 12/2001 | Mian et al. ................... 436/45 |
| 2008/0214412 A1 * | 9/2008 | Stahler et al. ................. 506/30 |

FOREIGN PATENT DOCUMENTS

| | | |
|---|---|---|
| EP | 0 950 890 | 10/1999 |
| JP | 3 252556 | 11/1991 |
| JP | 4 252957 | 9/1992 |
| JP | 6094724 | 4/1994 |
| JP | 9509498 | 9/1997 |
| JP | 10 505672 T | 6/1998 |
| WO | WO 96/14934 | 5/1996 |
| WO | 97/07390 | 2/1997 |
| WO | 97/34139 | 9/1997 |
| WO | WO 98/07019 | 2/1998 |
| WO | 98/15810 | 4/1998 |
| WO | WO 9815810 A1 * | 4/1998 |
| WO | 98/50777 | 11/1998 |

* cited by examiner

METHOD FOR THE ASSESSMENT OF PARTICLES AND A SYSTEM AND DEVICE FOR USE IN THE METHOD

This is a continuation of application Ser. No. 09/830,557 filed May 7, 2001.

FIELD OF THE INVENTION

This invention relates to a method, a system and a device to be used in the determination or assessment of at least one quantity parameter and/or at least one quality parameter of particles in a liquid analyte material. As an important quantity parameter can be mentioned the number of particles in a volume of the analyte material, such as, e.g., the number of somatic cells in milk or blood, or the number of bacteria in a urine sample. Another important example of a quantity parameter whether or not an analyte, such as a liquid analyte derived by selective enrichment of a food sample, contains a particular bacterial species, such as *Salmonella typhimurium*. As examples of quality parameters may be mentioned morphological properties of particles such as size and/or shape, or identification of one or more types of particles in a mixture of more than one types of particles. In the following the term "partides" is used in a broad sense, referring to objects (e.g. cells or cell fragments, bacteria or bacteria fragment, macromolecules or macromolecule fragments such as proteins or DNA/RNA, polymer beads or fragments of polymer beads) or phenomena (e.g. concentration of molecules, physical or chemical gradient) which, when used in combination with the present invention, can interact with, transmit, emit or attenuate electromagnetic irradiation which can be detected as an image, either due to one or several inherent properties of the partide or due to chemical or physical modification of the particle. Such particles can be present in the volume of the analyte material prior or during analysis, or the particles can be formed prior to, or during analysis.

DESCRIPTION OF THE RELATED ART

Determinations or assessments of the above types have been performed by various methods. One of these methods is flow cytometry; instrument for performing flow cytometry are available, e.g., from Becton, Dickinson and Company, Franklin Lakes. Great care is needed in sample preparation and the results obtained are highly dependent on the sampling handling taking place within the flow cytometer instrument The sample being analysed is passed in a thin stream sheded in a broader stream carrier stream, the dimension of the analyte stream preferably being such that substantially only one particle of interest is in the view of the detector at a time. In particular it is necessary to control the flow of the sample material during the measurement in order to be able to relate the observed result to the volume of the sample being analysed.

Another known method for the determination of somatic cells or bacteria in milk is based on the detection of signals from particles which are dispersed on the rim of a polished rotating disc, one such instrument available from Foss Electric, Hillerod, Denmark. The accuracy in the assessment of the number of particles using this method is dependent on the physical shape of the thin film of sample dispersed on the disk, and high sensitivity is needed to detect the weak signals from the particles in question in the course of the relative short period of time the particle is present in the detector. The arrangement of the sample on the rim of the rotating disc is preferably such that only one particle of interest is in the view of the detector at a time.

Due to the relative high complexity and cost of the instruments used today, most of the assessments of particles are carried out on in a laboratory where skilled operators operate the instruments.

DESCRIPTION OF THE INVENTION

This invention extends the capabilities of prior devices and methods to enable more simple and reliable assessment of particles in liquid analyte material. The properties which can be assessed are the number of particles in a volume of the analyte material, any morphological properties such as size or area of the particles, or the identification of the type of particle being analysed. In particular it is possible to assess more than one of these properties simultaneously.

At the same time, this invention allows these analysis to be carried out with the use of considerably smaller amounts of sample material and any added chemicals than normally are required to do these analysis. These chemicals are often considered hazardous, either to humans and other living organism or to the environment. Furthermore, this invention presents a solution of the safe handling of sample and reagents with the use of a substantially sealed device which contains all sample material and chemicals used for the assessment and allows save transport of the sample and any chemicals.

The high cost as well as the mechanical complexity of the instruments hitherto used for the routine assessment of particles in liquid analyte material has made the instruments impractical to use routinely under condition such as are normally present outside the environment of a specialised laboratory, such as on dairy farms, on milk dairies, or in medical or veterinary clinics. Such analyses are of great interest, for instance, a dairy farmer can monitor the somatic cell count or bacterial count of an individual animal in order to follow the course of clinical or subclinical mastitis or infection. and to control the cell count of the bulk milk delivered to the dairy, thereby minimising the use of antibiotics and preventing the economical penalty which is often a consequence when the cell count of bulk milk exceeds predefined limits.

Medical and veterinarian clinics are often in the need to know the count of one or more particles in blood, urine or other fluids such as somatic cells or bacteria, but since such analysis are usually carried out in a central laboratory, this often delays the response of such analysis due to transport of the sample. The present invention allows the construction of more simple analytical instruments which are well suited for use in medical and veterinarian clinics and the like, to be operated by operators after only limited training.

This invention allows the analysis of various types of particles, such as DNA-containing particles, DNA molecules or fragments thereof, red blood cells, blood platelets, yeast cells, bacteria cells, lipid globules, protein micelles and/or molecules, antibody/antigen particles, dust particles, or polymer particles, these particles normally present in and/or added to liquid biological analyte material such as milk, blood, urine, faces, salvia, inflammation, of either human or animal origin, or samples originating from the petrochemical industry, the pharmaceutical industry, feed industry, food industry, water supply industry or the like. The device is also well suited in the detection of any other biological particle or fragments thereof, such particle being a part or a fraction of living matter and displaying properties which can be detected with the detection of electromagnetic radiation.

This invention is particularly suited for the assessment of the number of somatic cells In milk from human, cow, goat, sheep, buffalo or other animal. Furthermore, the invention is particularly suited for the assessment of the number of cells in blood, such as human blood. In particular, the number of various somatic blood cells may be assessed.

The liquid sample representing the analyte material may be a liquid sample consisting of the liquid analyte material per se (optionally and often preferably with added chemical substances facilitating the assessment, such as will be explained in the following), or it may be a sample which has been derived from the liquid analyte material by dilution, concentration, extraction, or other modification. In this connection it is, of course, normally essential that there is an unambiguous correlation between the volume of the liquid sample representing the liquid analyte material and the volume of the liquid analyte material in question, so that the necessary correlation to a concentration in the liquid analyte can be established. As mentioned above, the liquid analyte material may in itself be a derivative of another material the properties of which are to be analysed using the method of the invention; thus, e.g., the liquid analyte may be a liquid enrichment culture derived from a food product, e.g. poultry.

Alternatively, particles isolated from a volume of a liquid sample representing the liquid analyte material may be the material from which the exposure of electromagnetic signals is made. This is the case, e.g., when a liquid sample representing the liquid analyte material has been filtered through a filter material, and the filter material with the retained particles, often after addition of chemicals facilitating the assessment, cf. below, such chemicals having been added before or normally after the filtration, is arranged in the sample compartment from which the exposure is made, normally a sample compartment suited for housing the filter.

This invention allows the sample material to be a substantially aqueous solution, or substantially organic solution, or a mixture of two or more inmiscible phases, some of which can be liquid, some of which can be solid and some of which can be a suspension, into which the particles of interest are suspended. In many preferred embodiments of this invention the sample material to by analysed has been modified or its chemical or physical properties substantially changed compared to the analyte material by either the addition of, or the removal of one or more components, or by introducing the sample to one or more chemical, mechanical or physical treatments prior to analysis. Preferably the effect of any such alteration or modification is the enhancement of any exposed signal used for the analysis, or a suppression of any interfering phenomenon, or it has the effect of prolonging the working life of the sample.

Methods according to the invention are suited for the on-line or at-line assessment of the number of somatic cells in milk when the purpose is to establish information about the health status of animals, such as cows, goats, sheep or buffaloes, especially in connection with clinical or sub-clinical mastitis.

The method according to the invention is suited for the assessment of the number of somatic cells in milk when the objective of the analysis it to generate information used in a heard improvement scheme, or when the objective of the analysis is to obtain a quality parameter used in a payment scheme. These analyses are today normally carried out on a central laboratory, by the use of complex instruments.

The present invention is based on the arrangement of at least a part of the sample in such a manner that it extends over a "window" of the device of a substantial area and allows the exposure of signals from the samples in the form of an "image". When the image is to be detected, the device, or at least a part of a window part of the device, is in an engagement with a detection device or an instrument comprising detection means. The engagement is normally the action of placing at least a part of the window in the sensing domain of the detection device, for instance by sliding the device into the sensing domain using one or several guides which at least approximately assure the correct arrangement of the window in the sensing domain. The placing of the device in engagement with the detection device would often be done manually, but in embodiments where the speed of operation and/or the precision of the placing of the device is of importance, the placing of the device could be done automatically, or at least semi automatically, where the placement is performed or controlled by mechanical and/or regulating means.

The image which can be detected from the window of the device can for instance be detected by an array of detection elements, the array of detection elements comprising individual elements each of which is capable of sensing signals from a part of the sample window area, the array as a whole being capable of sensing signals from substantially ail of the sample window area, or at least a well defined part of the sample window area.

As will appear from the following, the arrangement of the sample in the device allows the assessment the particles in a simple and economic manner, while retaining a high accuracy of the determination.

An aspect of the invention relates to a method for the assessment of at least one parameter of particles in a liquid analyte material, comprising providing a device comprising a sample compartment with an exposing domain, an inlet through which a volume of a liquid sample representing the analyte material can been introduced, and a flow system comprising at least a channel allowing at least a portion of the volume of the liquid sample to flow within the device, Introducing a volume of the liquid sample in the device through the inlet of the disposable device, passing at least a portion of the volume of the liquid sample through the flow system of the device into the exposing domain of the sample compartment.

arranging the device in relation to a detection device comprising detection means for quantitatively detecting spatial image data and processing means for processing the detected image presentation detecting electromagnetic signals from the sample in the exposing domain of the device in the detection device forming, in the detection device, a spatial image representation of the exposing domain, and processing the detected image presentation obtaining the assessment of the at least one parameter.

By the term "exposing domain" is meant a compartment or an equivalent thereof in which the part of the volume to be assessed is located during the assessment The parameter to be assessed is preferably the number of the particles also designated a quantity parameter, the morphology of the particles, the viability of the particles, and/or the DNA content of the particles, also designated quality parameters.

The term a portion of the volume is meant to include either a portion having corresponding composition as the total volume or a portion having another composition, such as a portion preferably being enriched in particles.

Another aspect relates to a system for the assessment of at least one parameter of particles in a liquid analyte material, comprising a device comprising a sample compartment comprising an exposing domain, an inlet through which a volume of a liquid sample representing the analyte material can been introduced, and a flow system comprising at least a channel allowing at least a portion of the volume of the liquid sample to flow within the device,.

a detection device comprising detection means for quantitatively detecting spatial image data and processing means for processing the detected image presentation, the device and the detection device having means for arranging the device in relation to the detection device in a manner allowing electromagnetic signals from a sample in the exposing domain of the device to pass to the detection device and to form, in the detection device, a spatial image representation of the exposing domain.

The flow system according to the invention provides at least one of several operations to be carried out on the samples, said operations being selected from but not limited to transport, mixing with reagent, homogenising of sample and optionally reagent, heat treatment, cooling, sound treatment, ultra sound treatment, light treatment and filtering.

Another aspect relates to a device adapted to be used in a system for the assessment of at least one parameter of particles in a liquid analyte material, the a device comprising a sample compartment comprising an exposing domain, an inlet through which a volume of a liquid sample representing the analyte material can been introduced, a flow system comprising at least a channel allowing at least a portion of the volume of the liquid sample to flow within the device, and means for arranging the device in relation to a detection device, which detection device comprises detection means for quantitatively detecting spatial image data and processing means for processing the detected image presentation in a manner allowing electromagnetic signals from a sample in the exposing domain of the device to pass to the detection device and to form, in the detection device, a spatial image representation of the exposing domain processable by the processing means of the detection device.

The device is preferably a disposable device, and in the present context, the term "disposable" indicates that the device in question is adapted to be discarded, or disposed of, after the detection has taken place in the analysis of one sample or a few, often a predetermined number of times. For certain embodiments of the invention, however, in particular where the device contains several sample compartments, the device could be used for several samples, and this could be performed either as one operation or as a series of sequential operations.

The term arranging in relation to means that the device is situated in or engaged with the detection device in a manner whereby the signals from the exposing domain are capable of being exposed to the detection device The disposable device constitutes a unit which should preferably be made available to the users at low cost, but at the same time, should by no means detract from the accuracy of the determination or assessment According to the invention, it has been found that it is indeed possible to obtain a very high accuracy of the determination or assessment using disposable devices of designs which will permit both an economic production and the use of small to very small sample sizes.

in case the disposable device is prefilled with reagent, the disposability may relate to the reagent being consumed. For some embodiments, the devices are constructed without a sample outlet, whereby the sample remains in the device after the assessment has taken place. The sample may remain in the sample compartment or be transported to a final compartment. In any case, the device is disposable either after one or a few samples being assessed. When the sample remains in the device, no contamination of the environments due to the sample or sample-reagent mixture is risked.

Furthermore, the sample, after being introduced to the device, may be stored, for example in a freezer, for later re-assessment or inspection.

Figure 1:
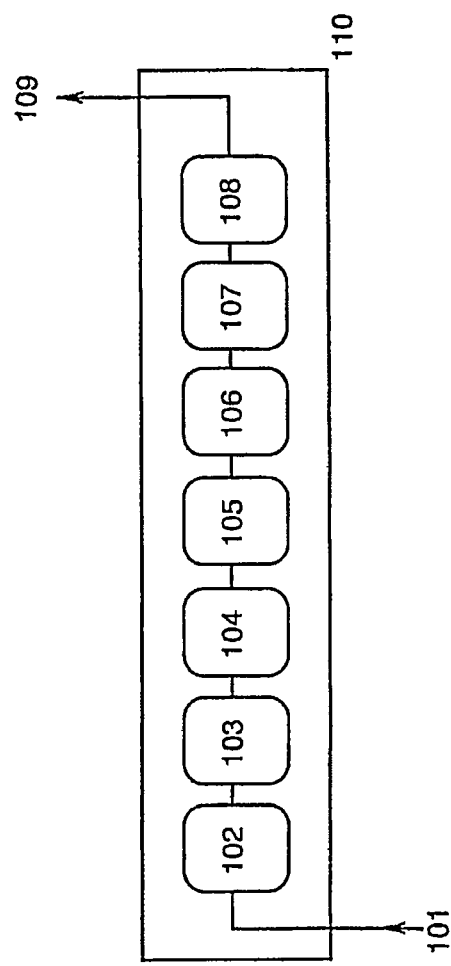
FIG. 1 illustrates the components of a disposable device

DETAILED DESCRIPTION OF THE INVENTION in connection with many embodiments of the method of the invention, the particles the parameter or parameters of which are to be determined are not in themselves capable of emitting or interacting with an electromagnetic irradiation in a way which could be used as a basis for the image generation and it is therefore, often necessary to add one or more components, in the following called reaction components, to the liquid sample prior to the detection. Preferably the addition of one or more reaction components to the liquid sample is performed in the device. It is often preferred that the signal which is emitted from the device is a photoluminescence signal, originating from a molecule, or a fraction of a molecule having fluorophor properties, naturally contained within or on the particle which is measured.

The signal which is emitted from or transmitted through the device often originates from, or is modified by, one or several types of molecules of types which bind to, are retained within, or interact with, the particles, such molecules being added to the sample or the isolated particles before or during exposure, the molecules being molecules giving rise to one or several of the following phenomena: attenuation of electromagnetic radiation, photoluminescence when illuminated with electromagnetic radiation, scatter of electromagnetic radiation, raman scatter. In the presently most preferred embodiments an effective amount of one or more nucleic acid dyes and/or one or more potentlometric membrane dyes is added.

For example, a particularly important example is a fluorochrome which can be bound to, or retained within, relevant particles so that the particles, upon excitation with a suitable source of electromagnetic irradiation, will emit an electromagnetic irradiation on the basis of which the image can be generated. Such reaction components can suitably initially be loaded in a compartment or flow channel part of the flow system of the disposable device from where they can be added to at least a portion of the volume of the liquid sample representing the analyte material.

The reaction components, which normally comprise one or more chemicals, are preferably initially loaded in the compartment or flow channel part in solid form. As solid forms of the reaction components may not be easy to dissolve as fast and as efficiently as is necessary for a realistic operation of devices according to the invention, it is often preferred that the reaction components comprise one or more chemicals in solid form in combination with one or more solubilising agents aiding the solubilisation of the chemicals in the liquid sample.

A very suitable solid form of the reaction components is the freeze-dried form which, because of its high surface area and incorporated solubility enhancing substances show a very high rate of solubility.

in another embodiment the addition is performed by introducing first said liquid sample and afterwards introducing the reaction components. In this embodiment reaction components are mostly on liquid form.

The amounts and availability (solubility and/or dispersibility in the liquid sample under the conditions prevailing) of the reaction components and the design of the flow system are preferably so adapted that a predetermined minimum of the reaction components will be contained in the liquid sample present in the sample compartment.

Often, it is of interest to form and detect signals which can be attributed to, or are caused by one or several molecules or reaction components which bind to, are retained within, or interact with the particles. The number of different types of molecules (reaction components) added depends on the complexity of the assessment, and on the nature of the particles and sample material being analysed. It is for instance often advantageous to use two or more, such as three or even four types of molecules when the assessment concerns the identification of two or more types of particles, where the different particles interact differently with the different molecules, for instance by giving rise to a fluorescent signal at different wavelength. Often the addition of such two or more types of molecules is done simultaneously, but under some conditions it is preferred to add the molecules at different times. These added molecules can interact with the particles for instance by being retained within them, interacting with them or being prepelled by them or in any way alter the properties of the particles or the sample.

The preferred amount of any chemical component contained in the device prior to analysis can be varied according to the properties of the particles being assessed. Of the amount can be more than 30 μg per ml of the sample, but often it is preferable to have amount of less than 30 μg per ml of the sample, even less than 10 μg per ml of the sample. Some aspects of this invention allow an amount of less than 1 μg, or even less than 0.1 μg per ml of the sample.

The preferred molecules which can give rise to one or several of the following phenomena: attenuation of electromagnetic radiation, photoluminescence when illuminated with electromagnetic radiation, scatter of electromagnetic radiation, raman scatter. Reaction components suited for this purpose are for instance one or more nucleic acid dyes and/or one or more potentiometric membrane dyes. The amount of the reaction components can vary depending on the nature of the particle and the characteristics of the detection device, but an amount of 0.3-30 μg per ml of the sample would normally be adequate to form signals which can be detected by the detection device. As example of preferred reaction components which can be used to form signals which allow assessment of particles are one or more nucleic acid dyes which is/are selected from the group consisting of: phenanthridines (e.g. ethidium bromide CAS#: 1239-45-8, propidium iodide CAS#: 25535-16-4), acridine dyes (e.g. acridine orange CAS#: 65-61-2/CAS#: 10127-02-3), cyanine dyes (e.g. TOTO™-1 iodide CAS#: 143 413-84-7-Molecular Probes, YO-PRO™-1 iodide CAS#: 152 068-09-2-Molecular Probes), indoles and imidazoles (e.g. Hoechst 33258 CAS#: 023 491-45-4, Hoechst 33342 CAS#: 023 491-52-3, DAPI CAS#: 28718-90-3, DIPI (4',6-(dilmidazolin-2-yl)-2-phenylindole)). In particular it is found that the nucleic acid dye propidium iodide (CAS#: 25535-16-4) is suited for many assessment of DNA containing particles due to the fluorochrome properties which the molecule shows. When the reaction component is a potentiometric membrane dye it can be one or seceral of the following, but not limited to: Rhodamine-123, Oxanol V. When performing a quantitative assessment of particles it is normally necessary to control the addition of any component to the sample, in order not to affect the result of the assessment, for instance due to variation in dilution. The present invention offers embodiments where such requirements are less important than under conventional situations. This can be accomplished by introducing the components on a form which has only limited effect on the assessment, such as introducing any component as solid matter, thereby substantialty not altering the volume of any sample being analysed.

To further enhance the property of any reaction component used to form signals which are detected, or to assure more reliable interaction between the reaction components and the sample or the particles in the sample it can be of interest to add reaction components, which often are not the direct source of the signals formed but rather have influence on the signals being formed. One such reaction component, well suited for the assessment of cells or bacteria is TRITON X-100 $(C_{14}H_{22}O(C_2H_4O)_n)$, a nonionic surfactant available from the Dow Chemical Company, which has a hydrophilic polyethylene oxide chain (on average it has 9.5 ethylene oxide units) and an aromatic hydrocarbon lipophilic or hydrophobic group.

Often the reaction components have limited speed of salvation or dispersion in the sample, considering the time used for the mixing of sample and the reaction components. It is therefore of interest to be able to improve the speed of salvation or dispersion of the reaction components, either by having the reaction components on a form which allow relatively high speed of salvation or dispersion, e.g. by introducing the reaction components in a solution or on a freeze dried form, or by adding one or more components which aid the reaction components. The addition of one or more components could have the effect of either control the form the other reaction component have and/or directly taking place in the dissolution or solvation of the reaction components. Such components having effect of increasing the rate of dissolution or solubilisation of any chemical on a substantially solid, and/or substantially non-aqueous, and/or substantially freeze dried form, are preferably one or more types of organic or inorganic salts.

Depending on the property of the flow system of a disposable device and/or the reaction components used, there are virtually unlimited number of different reactions which can take place within a disposable device. It would for instance be of great interest to carry out one or more antibody/antigen reactions, preferably also involving polymer beads such as paramagnetic beads, and thus for instance obtain improved accuracy in the Identification of one or more types of biological particles such as cells, bacteria and proteins.

In a preferred embodiment of the invention the device contains at least one compartment containing chemicals which allows the mixing of the sample material with a solid or liquid material.

The device may comprise several reagent compartments to be used in series for the assessment of several samples or sequential addition to one sample. The several compartment can also be used in parallel for the substantially simultaneous assessment of several samples.

In order to assure fast assessment of a sample it is of interest to be able to perform analysis shortly after the mixing of any chemical components with sample. This time should therefore be less than 60 seconds, or preferably less than 30 seconds or even as low as 15 seconds and in other preferred situations as low as 10 seconds, and preferably as short as 2 seconds or less and even shorter than 1 second.

One preferred method for theintroduction of chemical components to the sample within the device is to place one or more chemical component in a container on a solid form. In order to allow rapid dissolving of any such chemicals on a solid form it is often preferred to mix it with a second chemical component, preferably one which can aid the rate of solubility of the chemical in question. Another preferred method of introducing such chemicals is to have them as freeze dried matter.

Often it is found that especially in relation to mixing a reaction component and a sample material, that gradients of chemical or physical property are formed. Such gradient being defined in the way that when it is possible to define at least two infinitively small parts or sections of the liquid matter within the device which are positioned immediately adjacent to each other witch have different chemical or physical property, such as chemical concentration of at least one chemical component, or temperature or viscosity being different in the two parts or sections of the liquid material. Such gradients can be observed in the longitudinal direction of a flow system, defined as parallel to the main direction of flow and/or in a radial direction, defined as perpendicular to the main direction of flow.

Even though it is often of interest to preserve longitudinal gradients in the flow system, it is preferred that such gradients can be eliminated or at least substantially reduced, for instance by passing the liquid sample through a part of a flow channel of the flow system of the disposable device having a shape and/or size resulting in substantially reduction of longitudinal gradients in liquids passing therethrough. In the present invention this can be accomplished when at least a part of the flow channel is a flow channel providing substantial laminar flow therethrough and/or comprising one or more mixing chambers.

Similarly, any radial gradient present in the liquid sample in the flow system can be substantially reduced by passing the liquid sample through a part of a flow channel of the flow system of the disposable device having a shape and/or size resulting in substantially reduction of radial gradients in liquids passing therethrough. In the present invention this can be accomplished when at least a part of the flow channel has at least one bend or obstruction resulting in substantially turbulent flow in the liquid passing the bend or obstruction.

In order to flow the sample into or within or out of the disposable device it is preferred to have at least one propelling means provided in the disposable device or in a device with which the disposable device can be engaged. In the latter embodiment it is to be understood that the liquid sample is introduced into the device after engagement with the detection means.

In particular it is of interest that the propelling means is provided in an adapter device with which the disposable device is engaged during liquid sample acquisition or even more preferred that the propelling means constitutes an integrated part of the disposable device.

Due to several aspects of any propelling means or the disposable device or the sample analyte material it is preferred that the velocity of the flow into, within, or out of the disposable device is regulated by means of one or more regulating means constituting part of the flow system. Such flow regulating means could be one or more of the selection of stop valves, one way valves, and pressure and/or speed reduction valves.

Preferably the flow regulation means is arranged to function stepwise so that the sample and/or the reagent component may be flowed stepwise through the device. It is furthermore preferred that at least the step of flowing the sample into the exposing domain is carried out in connection with the engagement of the device into the system.

The sample in the device can be flown by the means of a flow system, which can be driven by a pump or a pressurised gas, preferably air, or by causing a pressure difference such that the pressure on the exterior of the inlet is higher than the pressure within at least a part of the device thus forcing the sample to flow though the inlet. In many embodiments of the present invention the flow in said flow system is controlled by one or more valves which can adjust the flow speed of the sample.

In many preferred situations the flow of liquid in the device can be brought about by a vacuum, the vacuum being applied from a reservoir, preferably contained within the device. The vacuum can be established by a mechanical or physical action creating the vacuum substantially simultaneously with the introduction or the movement of the sample. These mechanical or physical actions can be: a peristaltic pump, a piston pump, a membrane pump, a centrifugal pump and a hypodermic syringe.

When flow only in predominately one direction is preferred, it is of particular interest to use valves which substantially only allow the flow in one direction. Such valves can for instance be placed up- and/or downstream from the sample compartment thus allowing the controlling of the flow condition in the sample compartment One effect of the use of such valves could be to confine at least a part of the sample in the flow system.

The outlet from the sample compartment can be passed through a flow controlling means, such as a valve, which only allows gas to pass through. One such type of valves which often is preferred, is one which allows gas and air to pass but can dose irreversibly when the valve comes in contact with liquid sample. The effect of such valve is to minimise the movement of any sample within the sample compartment during analysis.

The flow channels, in which the sample flows within the device can be formed in a number of different ways both with regard to shape and size. The effect of any mixing of a sample or any gradient of chemical or physical property can be substantially controlled by different shape and size of the flow channels. Assuming predominantly laminar flow, channels with large area of cross section will generally have the effect of allowing the sample to be mixed in the direction of the flow partly due to variation in the flow velocity across the cross section. On the other hand, channels causing the flow to rapidly change direction can substantially cause mixing of the sample in a direction predominantly perpendicular to the direction of the flow. Other properties of a flow channel can have similar effect, depending on the nature of the sample and/or the flow conditions used.

Depending on the nature of the sample analyte material and/or the assessment of the particles it is often preferred that the liquid sample is subjected to one or more operations selected from the group consisting of filtration, concentration and magnetic attraction, preferably the disposable device comprising the means for performing such operation or operations.

In many of the preferred embodiments of the invention the disposable device and its operation and the operation of the combination of the detecting device or devices with the disposable device engaged therewith are adapted so that the sample contained in the exposing domain permits a reproducible determination or assessment of the parameter or parameters to be determined or assessed. Similarly it is often preferred that the sample in the exposing domain permit the formation of a spatial image presentation the background of which is within the operational dynamic limits of the detection device, and the sample is in substantial spatial equilibrium throughout the volume of the exposing domain during the detection. By the term substantial spatial equilibrium is meant that a still image is obtainable from the sample. On the other hand, many embodiments of the present invention permit that the sample in the exposing domain permit the formation of a spatial image presentation the background of which is within the operational dynamic limits of the detection device, and the sample in the exposing domain is not in substantial equilibrium throughout the volume of the exposing domain during the detection, the detection and the processing of the image data substantially securing distinction between particles and background.

In order to allow reproducible and reliable assessment of particles it is preferred that the design and the production of the disposable device is such that any dimensions of the disposable device which influence the volume of sample represented in the spatial image representation are kept within predetermined variations from device to device. On the other hand some aspects of the design and the production of the disposable device can be such that variations between individual disposable devices in dimensions which influence the volume of sample represented in the spatial image representation cannot be kept within predetermined variations, but are indicated on the disposable devices in that each disposable device is associated with information as to data concerning the dimensions in question, and the information is taken into consideration in the processing of the detected image presentation. In particular it is preferred that such information as to data concerning the dimensions in question is contained in insignia carried by the disposable devices and readable by the detection device or another device adapted to read the insignia.

In order to make use of the information of the variation of one or more dimensions the data concerning the dimensions in question are transferred to the processing means of the detection device to enable the processing means to take the data into consideration in the processing of the detected image presentation. It is preferred that the transfer of the data to the processing means is performed automatically or through human interaction. If the transfer of the data to the processing means is performed automatically it is often only performed when an authentication insignia has been identified. Normally such authentication insignia is an image or other insignia proprietary to a producer or distributor of the disposable devices authorised by a private or official body to provide the disposable devices for the determination or assessment in question. Further more, the authentication insignia can comprise of encrypted information or a trademark and the detection device or other device is capable of decrypting the encrypted information or identifying the trademark.

In embodiments of the invention variations in dimensions of the disposable device which influence the volume of sample represented in the spatial image representation are compensated in the assessment on the basis of volume calibration means. Often such volume calibration means is constituted by one or more of the reaction components, in which case the reaction component or components in question is/are loaded in a predetermined concentration, and the flow operation of the device is performed in a manner ensuring that the predetermined concentration will be reflected in the concentration of the reaction component or components in the exposing domain. In other embodiments of the invention variations in dimensions of the disposable device which influence the volume of sample represented in the spatial image representation are compensated in the assessment on the basis of one or more reaction components and/or diluents which have been added to the sample, and the proportion of the volume of sample in the exposing domain which corresponds to the original sample representing the analyte material is assessed by detecting and processing one or more signals substantially originating from the one or more reaction components and/or diluents added.

The detection of the spatial image representation of the exposing domain of the disposable device is preferably performed by means of an array of active detection elements onto which array the spatial image presentation is exposed. In order to facilitate the assessment of particles the intensities detected by the array of detection elements are processed in such a manner that representations of electromagnetic signals from the particles are identified as distinct from representations of electromagnetic background signals.

As discussed above some of the particles of interest show properties which can be used to form and detect a spatial image without substantially any addition of any reaction component. The signals which often can be formed and detected in this manner are signals which are substantially caused by attenuation of electromagnetic signal, and/or by emission of electromagnetic irradiation by photoluminescence. The attenuation of signals and/or the photoluminescence signals being associated to one or more molecules which is/are a part of the particle, preferably where the particle is somatic cell or bacteria and where the molecules are DNA and/or proteins as described above.

In many advanced embodiments of the present invention it is possible to determine the amount and/or the level of any constituent in a sample material, preferably substantially simultaneously with the assessment of particles, and the constituent being determined could be, e.g., one or several of: fat, protein, lactose, urea, citric acid, glucose, ketones, carbon dioxide, oxygen, pH, potassium, calcium, sodium. The determination of a component can be done in a sample compartment or a domain, often the same sample compartment or exposing domain which is used for the assessment of particles. The methods used for the determination could be based on spectrophotometric measurement, the spectrophotometric measurement being, e.g., one or several of; mid-infrared attenuation, near-infrared attenuation, visible attenuation, ultra-violet attenuation, photoluminescence, raman scatter, nuclear magnetic resonance. Other methods also suited for the determination of any chemical property could based on potentiometric measurement, preferably by the use of ion selective electrode.

It is often of interest to minimise the use of any sample material and any chemical component used for the analysis, for instance when the sample material or any chemical reagent can be considered hazardous or when it is difficult to obtain in large quantity. This can be accomplished by the use of the present invention. Sample volumes as small as 1 ml or less and even as small as 0.02 ml can be used. The optimal volume of the sample needed is highly dependent on the number of particles present in the sample and the predetermined statistical quality parameter sought.

Other preferred embodiments of the present invention make it possible to assess particles from a considerably large volumes of sample. This can allow the measurement of samples with only few particles of interest per volume of sample. Sample volumes larger than 1 ml and even larger than 100 ml can be used for the analysis, the volume being defined as the total volume of any liquid sample introduced to any flow system connected to the device before the measurement of the sample.

Often the design of the sample compartment or the exposing domain of the disposable device is such that the size of the volume of the liquid sample is sufficiently large to permit the assessment of the at least one quantity parameter or the at least one quality parameter to fulfill a predetermined requirement to the statistical quality of the assessment based on substantially one exposure.

In many assessments of particles it is of interest to allow exposure of signals from substantially large volumes of sample. The volume of the liquid sample from which signals such as electromagnetic radiation is exposed onto the detection system is normally in the range between 0.01 µl and 20 µl. Generally the volume of the sample being analysed should be as large as possible. This allows the simultaneous assessment of a higher number of particles, but the optimal volume is often defined by one or more aspects of the detection system and the sample being analysed. Thus the volume of the sample in the sample compartment can be less than 0.1 µl but often volume of more then 0.1 µl, 1.0 µl or even 10 µl is used. In still other application volume of the sample compartment as large as 100 µl or more can be used.

Although device may be used in method using a high degree of enlargement of the image projected to the detection elements, such as 1:10 or even 1:40, the device is especially suitable for use in a method wherein the degree of enlargement is around 1:1, such as 1:2 or 1:4.

As mentioned above, it is one of the characterising features of the present invention that a relatively large volume of sample can be exposed to the detection system. The sample is contained in the interior of the sample compartment, which normally has an average thickness of between 20 µm and 2000 µm, usually between 20 µm and 1000 µm and in many practical embodiments between 20 µm and 200 µm. In the present context the term "sample" does not necessarily mean the sample present in the compartment, but rather the sample introduced into a flow system used according to the invention. It is of interest to minimise the use of sample material and any chemical component used for the analysis. This can be accomplished by the use of the present invention. Sample volumes as small as 5 ml or less and even as small as 0.02 ml can be used. The volume of the sample needed is highly dependent on the number of particles present in the sample and the predetermined statistical quality parameter sought, whereby typical volumes applied is less than 5 ml of a liquid sample, preferably by using less than 2 ml of a liquid sample, more preferably by using less than 1 ml of a liquid sample, more preferably by using less than 0.5 ml of a liquid sample, more preferably by using less than 0.2 ml of a liquid sample, more preferably by using less than 0.1 ml of a liquid sample, more preferably by using less than 0.05 ml of a liquid sample, more preferably by using less than 0.02 ml of a liquid sample, more preferably by using less than 0.01 ml of a liquid sample, the volume being defined as the total volume of any liquid sample introduced to the sample compartment, or any flow system connected to the sample compartment before or after or during the measurement of the sample.

Normally, the sample compartment has dimensions. In a direction substantially parallel to a wall of an exposing window, in the range between 1 mm by 1 mm and 10 mm by 10 mm, but it will be understood that depending on the design, it may also be larger and, in some cases, smaller.

Thus the area of the exposing window can be as little as 0.01 $mm^2$ or more, preferably with an area of 0.1 $mm^2$ or more, more preferably with an area of 1 $mm^2$ or more, preferably with an area of 2 $mm^2$ or more, preferably with an area of 4 $mm^2$ or more, preferably with an area of 10 $mm^2$ or more, preferably with an area of 20 $mm^2$ or more, preferably with an area of 40 $mm^2$ or more, more preferably with an area of 100 $mm^2$ or more, preferably with an area of 200 $mm^2$ or more, preferably with an area of 400 $mm^2$ more, preferably with an area of 1000 $mm^2$ or more, preferably with an area of 2000 $mm^2$ or or more, preferably with an area of 4000 $mm^2$ or more, preferably with an area of 10000 $mm^2$ or more. Similarly, it is advantageous to extend the window of the sample compartment in a direction which is parallel to the plane of any window exposing signals from the sample to the exterior in order to extend the area of the exposing window and thus increase the volume of the sample which is exposed to the exterior.

A large volume of the sample is preferably measured by passing the volume of sample through a particle retaining means, such as a filter, electrical field, magnetic field, gravitational field, such means preferably being included in the device or can be arranged to interact with any sample within the device. The particle retaining means should preferably be able to retain substantially all particles present in a sample, or at least a substantially representative fraction of at least one type of particles present in the sample.

When the particles from a large sample are retained, those particles can be resuspended in a volume which is less than the volume of sample passed through the particle retaining means.

In one embodiment of the present invention a signal from the particles being analysed is detected while the particles are still substantially retained by a particle retaining means. In such embodiment the particle retaining means are integrated with, or in close connection to a sample compartment In many preferred embodiments of the present invention, at least one dimension of the sample compartment, as defined by the aspects of the detection system, could be so small that it could be difficult for the sample to flow into or through the sample compartment. By using one aspect of the present invention it is possible to vary at least one of the dimensions defining the sample compartment in such a way that the dimension is substantially greater during the flowing of the sample into or through the sample compartment than during the measurement of any signal from the sample. One effect of such a variation of at least one dimension of the sample compartment can be to partly or substantially completely replace the sample in the sample compartment between the measurement of any signal from the sample, substantially without introducing any other force on the sample in the device. It is of interest to vary the at least one dimension of the sample compartment in such a way that the volume during at least a part of any period when a sample is introduced to the domain is at least 10% larger than the volume during at least a part of any period when detection is performed, preferably where the volume is 25% larger. When considering applications where large difference in the dimension is preferred the volume is 50% larger, more preferably where the volume is 100% larger, more preferably where the volume is 200% larger more preferably where the volume is 400% larger. The shape and size of the sample compartment and/or any connected part of the flow system can be such, that the effect of varying the at least one dimension of the sample compartment is at least substantial replacement of part of a sample in the domain with a different part of the sample, allowing detection of signals from substantially different part of the sample.

Concerning the spatial definition of the shape and size of the area of an exposing domain or a window exposing signals to the detection device there are at least two feasible methods for substantially reliable definition of the size and shape of this area The first, and in many embodiments preferred method, is to adapt the detection device to be sensitive to exposed signals from a substantially defined area of the exposing window, e.g. by adapting any focusing means of the detection device. The second method, which is in particular preferred when it is difficult to adapt the sensing area of the detection device, is to define the boundaries of such exposing area of the sample compartment, e.g. either by controlling the dimensions of the sample compartment which define the exposing area, or by forming a mask or and effective window defining the exposing area, either in or on the disposable device or in connection with the detection device.

The requirements of the wall of the sample compartment are in particular that the wall allows the signals to pass without any significant limitations. In practice no upper limit is given for the wall thickness apart from what is defined by cost and design. The wall is preferably a substantially stable wall, which leads to a lower thickness limit for each material used. Preferably, the wall is from 0.1 mm to 2 mm, such as from 0.5 mm to 1.5 mm, more preferred from 0.75 mm to 1.25 mm.

In some embodiments, a flexible wall is useful, however, for quantitive measurements this will require measurement of the volume of the sample exposed before the assessment is carried out.

It is clear, that when simple operation of an instrument detecting signals exposed from the disposable device is desired, that it would be possible to have the bringing of the disposable device in engagement with the detection device activating the detection of any signals from the disposable device, and thus activating the assessment of particles forming signals in the sample compartment.

The device of the present invention, can easily be removed from a measuring instrument when a new sample or sample material is to be measured. Such removable device is preferably used for a limited number of measurements and preferably only one before being replaced with another device. Apart from allowing a more simple mechanical construction of an instrument used for the collection and analysis of exposed electromagnetic signals with the absence of any permanent flow system, one advantage of such removable device is that it can contain the sample in a closed container before, during and after analysis, thus allowing more safe handling of hazardous material. In many embodiments of the present invention such removable device can, prior to the introduction of any sample material, contain one or more components used for chemical or physical modification of the sample prior to analysis.

One important aspect of the present invention, which is particularly of interest when the sample, or any component added to the sample can be considered hazardous, or difficult to handle, is that it is possible to contain the sample within the device before, during and after the analysis. Prior to analysis the device, containing the sample, is introduced to a measuring system. After the analysis have been performed the device is readily removed from the measuring system, allowing another device to take its place. One interesting aspect of the present invention is the possibility of substantial irreversible sealing the device after the addition of a sample, thus preventing any accidental spill or leakage from the sample device during storing, transport or disposal.

When the device is intended to be destroyed or the material re-used after use it is preferred that the compartment is made up by a material which allows destruction by means such as burning or illumination by electromagnetic radiation. In the situations where the destruction comprises a re-use of the material from which the device is made of, a process of regeneration of the materials is preferred to comprise one or several of the following steps: emptying the device for any sample material or any other components, rinsing or washing, removal of one or more physical components of the device, replacing of one or more physical components of the device or addition of one or more chemical components.

The device is constructed of a material that has the sufficient physical strength as well as being capable of being shaped into the required physical and functional appearance. In particular, the material must be robust during storage, transport and use of the device.

Furthermore, the material must be compatible with the reagents used, in particular reagents prearranged in the device, so that the reagent cannot dissolve, react with or diffuse into the material within a predetermined period of time.

Whereas transparency is important for the wall art of the sample compartment where through the signals are passing the transparency of the rest of the device is of less importance, apart from situations where either the sample or a reagent is light sensible even for short exposures to light. Preferably the material contains substantially no fluorescence that would otherwise disturb the assessment.

In particular, a plastic material is useful such as a material selected from polystyren, polyester, polycarbonat or polyethylene.

The device is preferably constructed of a back side and a front side where each side may be moulded individually to be subsequent assembled. The sides of the device are preferably moulded from the same material.

The window area(s) of the sample compartment is/are preferably moulded separately to be inserted into the device parts before the final assembling.

In a preferred embodiment of the invention the particles being assessed are substantially at stand-still during analysis, thus allowing the optimal use of measurement time in order to improve any signal to noise conditions. This arrangement also eliminates any error which could be inherent in the assessment of particles caused by variation in flow conditions, particularly when an assessment of a property is a volume related property such as the-counting of particles in a volume of sample. However, in another embodiment, the sample in the sample compartment is moved through the sample compartment during the exposure, and the exposure is performed over a sufficiently short period of time to substantially obtain stand still condition during the exposure. In either case, there is a close control of the volume of the sample from which the exposure is made, which is one very preferred feature of the present invention.

One aspect of such removable device is that more than one portions of the same sample material can be subjected to analysis by exposure to the detection system. This can be done by allowing the sample compartment to be moved, thus exposing a different portion of the sample compartment, or by allowing the sample within the sample compartment to flow and thereby substantially replace any sample volume exposed with a different sample volume.

When at least a major part of the electromagnetic radiation emitted from the sample during exposure originates from or is caused by electromagnetic radiation supplied to the sample from a light source, it is highly preferred that at least a major part of the radiation from the light source having a direction which is transverse to the wall of the sample compartment or a plane defined by the sample compartment (or an increment plane if the compartment wall is curved), or between perpendicular and 10 degrees, preferably between perpendicular and 20 degrees, more preferably between perpendicular and 30 degrees and still more preferably between perpendicular and 45 degrees.

In a preferred embodiment, the backside wall of the sample compartment (i.e. opposite the wall through which the signals are passing) may be provided with a light diffusing effect. This may for example be provided by shaping this window area with a rough surface.

As mentioned above, the size of the volume is suitably adapted to the desired statistical quality of the determination. When considering the requirements to the size of the volume of the sample there it is often the nature of the analysis which defines such limits. Often the nature of the sample and the particle of interest in the sample which is to be analysed is one ore more of the following: I) The presence of a particle in a sample is to be determined. The assessment of the presence of the particle is done in relation to the volume since only rarely the entire sample represents the sample volume. II The particles of interest can be expected to be present in a number which are defined by both a low and a high limits. One example of this is the number of somatic cells in blood where the lower limit is substantially defined by the level at which the organism can sustain an adequate immune activity and the high limit is defined by the capacity by which the organism can produce the somatic cells. III The concentration of the particles of interest can be expected to be bound only by one limit, often high limit. One such example can be the number of somatic cells in milk, where there are situations where the lower limit is virtually indefinable while the upper limits are defined by the capacity by which the cow can introduce somatic cells to the milk.

The size of the volume which is preferably used for the analysis is therefore normally related to the conditions described above. Thus, where the determination is the determination of the number of particles in a volume, or the determination of the size and/or shape of particles, the size of the volume of the liquid sample is preferably sufficiently large to allow identification therein of lower limit of particles. For the individual applications of the present invention, it is possible to define a lower limit of particles to be relevant to assess and thereby a relevant size of volume to be assessed. This is in particular the case when assessing bacteria in the sample as well as cells such as somatic cells in the sample.

For some applications also an upper limit is definable, such as somatic cells in blood. Preferably, the size of the volume of the sample is large enough to allow identification therein of at least two partides with the desired statistical quality.

More preferably, the size of the volume of the liquid sample is sufficiently large to allow identification therein of at least four of the particles. This will correspond to a repeatability error of approximately 50%. Still more preferably, the size of the volume of the liquid sample is sufficiently large to allow identification therein of at least 10 of the particles. This will correspond to a repeatability error of approximately 33%. Even more preferably, the size of the volume of the liquid sample is sufficiently large to allow identification therein of at least 50 of the particles. This will correspond to a repeatability error of approximately 14%. Evidently, where possible, it is preferred to aim at conditions where the size of the volume allows identification of even higher numbers. Thus, when the size of the volume of the liquid sample is sufficiently large to allow identification therein of at least 100 of the particles, it will correspond to a repeatability error of approximately 10%, and when the size of the volume of the liquid sample is sufficiently large to allow identification therein of at least 1000 of the particles, it will correspond to a repeatability error of as low as approximately 3%.

A device comprising more than one sample compartments exposing signals from the sample could also allow the analysis of more than one portion of the same sample material, or the analysis of more than one sample materials.

One preferred implementation of the method is one which allows the substantially simultaneous assessment of more than one sample. This can be accomplished by placing two or more, or even four or more preferably independent flow systems, comprising at least one sample compartment each, in one disposable device. The signals from the two or more sample compartments can be measured one at a time, or two or more simultaneously.

This invention offers also methods for the assessment of particles in a removable device, where more than one such devices are loaded with sample and placed in a transport means which can move the individual devices in a position in a measurement system, preferably one at a time, which allows exposure of signals to the detection system. This allows substantial automation of the assessment of particles since more than one sample can be handled at once.

The invention allows analysis of various types of biological particles as described above and the invention is therefore particularly suited for the assessment of the number of particles in a liquid sample material in the following applications:

In particular in relation to analysis of milk samples, such as milk for dairy purposes, the invention is suitable. In milk the invention may be applied to analyse somatic cells, such as size and/or number of somatic cells in milk. Furthermore, the analysis may be carried out for bacteria in milk.

The milk may be analysed at any point of treatment of the milk, but the invention is particularly suitable for on-line or at-line analysis, wherein the milk is analysed during milking. The various operations incorporated into the device allows even persons not skilled in the art of laboraty techniques to perform valid results.

In relation to blood analysis the apparatus is suitable for all assessments on blood particles, such as the assessment of number and type of various blood cell types.

The invention may be used in laboratory or in general practice for cell counts and differential counts. Furthermore, the invention may be used by patients for example when controlling the total cell counts in connection with treatments, such as cancer treatment.

Urine samples may be analysed according to the present invention for bacteria, for example when assessment of total cell count is necessary in connection with urinary tract infections.

Also, the invention may be used when diagnosing specific cause of urinary tract infections, such as the bacteria type.

Assessment of particles in water may be conducted by the present invention, such as control of drinking water, control of waste water or water from a water purifying plant. In all applications the control may be related to the total particle count, such as bacteria count or it may more particularly be related to a monitoring process for specific bacteria, such as pathological bacteria.

With respect to assessment of bacteria the invention may also be used in connection with food or feed samples as well as petrochemical samples (eg for airplane fuel).

Furthermore, fermentation control, i.e. control of cell growth and viable cells in fermentation tanks may be conducted by the invention. This relates to all technical fields using fermentation, such as the pharmaceutical industry for producing peptide or protein composition.

A number of embodiment and variants of the invention appear from the figures and examples which follow.

With these and other objects in view, which will become apparent to one skilled in the art as the description proceeds, this invention resides in the novel construction, combination, arrangement of parts and method substantially as hereinafter described, and more particularly defined by the appended claims, it being understood that changes in the precise embodiments of the herein disclosed invention are meant to be included as come within the scope of the claims. The invention is now further described in relation to the drawings:

The components of a disposable device which can be used for the assessment of particles according to principles of the present invention are given in FIG. 1. The components in FIG. 1 are as follows:

An inlet 101 where the sample is introduced to the flow system, a pump 102 situated upstream from the sample compartment, a valve 103 controlling the inlet flow of the sample, means 104 allowing introduction of one or several intentionally added chemical components, means 105 which allow the mixing of the sample and one or several chemical components and/or any other mechanical or physical operation such as retaining particles, a sample compartment 106, a valve 107 controlling the flow from the sample compartment, a pump 108 situated downstream of the sample compartment, an outlet 109 from the flow system and a unit 110 housing one or several of the components of the disposable device.

Depending on the nature of the sample which is to be analysed and other factors associated with the sampling and measurement, the preferred disposable device would not always comprise all the components arranged as shown in FIG. 1, or one or more of the components could be integrated into one component. Below several possible constructions are discussed.

A Disposable Device Allowing Exposure of Single Volume of Sample

Several applications of the present invention can be based on a disposable device. Such a disposable devices will have a number of advantages, including the following: Elimination of a stationary flow system needed for the handling of any sample in an instrument that would need maintenance such as cleaning. The possibility of being able to sample and measure without any further handling of a sample, which makes the handling of hazardous material more safe since it could be possible to dispose of the device still containing any sample or reaction components, either by discarding it or by submitting it to controlled destruction or regeneration.

One such disposable device 110 is based on following components: An inlet 101 where the sample can be introduced to the disposable device, preferably a valve 103 close to the inlet or integrated with the inlet and allowing liquid sample to flow only in one direction, preferably a container 104 for any addition of reaction components, preferably a mixing chamber or a manifold 105 allowing the sample and any reaction components to mix, a sample compartment 106 where signals from the sample are transmitted to the exterior to be measurement by a detection device, a valve 107 controlling the flow of the sample through the sample compartment, preferably a valve which can allow gas or air to pass freely but which closes substantially irreversibly upon contact with the sample, and finally a pump 108 capable of propelling the sample from the inlet to, or past the valve 107.

When it is intended that any sample entering the inlet can be retained within the disposable device upon completion of the analysis, an outlet from the flow system unit through which the sample could leave the device will normally not be provided. Upon completion of the analysis, such a device can be safely disposed of or regenerated regardless of the nature of the sample and/or any reaction components added to the sample.

A Disposable Device for the Sampling of Large Volumes of Sample, Analysed by Multiple Exposure For some purposes, it may be interesting to be able to assess relatively large volumes of sample material by multiple measurements of a number of individual samples taken from a larger volume. This may, for example, apply when assessing the possible presence and, if present, the concentration, of bacteria which are objectionable even when being present in very small numbers, such as *Salmonella* in such as case, it may be of interest to perform a small, or a large, series of measurements of normal volume samples taken from a larger, but well-defined, volume of sample material, and then optionally relating the results from the small or larger series of volumes to the well-defined larger volume. According to the present invention, also this can be accomplished using a disposable device or a device which can be regenerated. There can be several advantages of such a device, including: improved sensitivity and precision due to multiple measurements and thereby assessment of a large total volume. Elimination of a stationary flow system which would need maintenance such as cleaning. The possibility of being able to sample once and then measure several times without any further handling of a sample makes the handling of hazardous material more safe.

One such disposable device 110 can be based on following components: An inlet 101 where the sample can be introduced in the disposable device, preferably a valve 103 dose to the inlet or integrated with the inlet and allowing liquid sample to flow only in one direction, preferably a container 104 for any addition of reaction components, preferably a mixing chamber or a manifold 105 allowing the sample and any reaction components to mix and having volume at least corresponding to the volume of the large sample with added reaction components, a sample compartment 106 of a normal volume where any signal from the sample is exposed to the exterior sequentially on a series of samples withdrawn from the large sample, a valve 107 controlling the flow of the individual sample through the sample compartment, and finally a pump 108 which, in connection with the individual measurements, is capable of passing at least a portion of the sample contained in the mixing chamber to the sample compartment for the measurement, the pump preferably having capacity to retain, in a large sample entering mode, at least the volume of sample entering the inlet.

The flow system would need the controlling of at least one valve and/or a pump allowing different portions of the sample to be analysed at a time.

A Disposable Device for the Sampling of Large Volumes of Sample Analysed by a Single Exposure It is often of interest to be able to assess a large volume of sample. Also this can be accomplished using a disposable device or a device which can be regenerated. The advantage of such device would include: improved sensitivity and precision due to assessment of a large volume of sample. Elimination of a stationary flow system that would need maintenance such as cleaning. The possibility of being able to sample and measure without any further handling of a sample makes the handling of hazardous material more safe.

One such disposable device 110 could be based on the following components: An inlet 101 where the sample is introduced in the flow system unit, preferably a pump 102 and/or a valve 103 close to the inlet or integrated with the inlet and allowing liquid sample only to flow in one direction, passing the sample to a particle retaining means (e.g. filter or magnetic force) or particle forming means (immobilised reaction component capable of binding to, or forming particles) 105 preferably containing means to hold at least the volume of sample entering the inlet, or connected to an outlet 109 allowing the sample to leave the flow system unit, preferably a container 104 for any addition of reaction components, connected to the particle retaining means, preferably a mixing chamber of manifold 105 allowing the sample and any reaction components to mix, a sample compartment 106 where any signal from the sample could be exposed to the exterior, a valve 107 controlling the flow of the sample through the sample compartment, preferably a valve which can allow gas or air to pass freely but closes substantially irreversibly upon contact with the sample, and finally a pump 108 capable of passing at least a portion of the sample contained in the particle retaining means through the chemical component container to the sample compartment for the measurement.

With slight variation in the arrangement of the components it would be possible to expose to the exterior signal from particles in the sample while still retained on or in the particle retaining means or particle forming means. One possible arrangement could be to include the particle retaining means or particle forming means in the sample compartment, and passing the sample through the sample compartment. Then preferably to pass any reaction component through or into the sample compartment to allow the mixing with any retained or formed particle and finally to detect any signals exposed from the sample compartment. In particular such device is well suited for the assessment of the presence of one or several type(s) of bacteria in substantially aqueous sample.

A Disposable Device for the Measurement of Several Samples

In many applications it would be of interest to be able to measure more than one sample without the replacement of any part of the flow system between analysis. Such a flow system could be a stationary part of an analytical instrument or it could be removed from the instrument between analysis.

One such disposable device could be constructed as follows: an inlet 101 where the sample enters the flow system and a pump 102 for the flowing of the sample, preferably a valve 103 for controlling the flow, preferably a reservoir for reaction components 104 which can preferably contain reaction components for the measurement of more than one sample, preferably a mixing chamber 105 for the mixing of the sample and any chemical component, a sample compartment 106 for the exposure of a signal from the sample, preferably a valve 107 controlling the flow of sample through the sample compartment, and possibly an outlet or a reservoir 109. In particular such device is well suited for the assessment of the presence of one or several type(s) of bacteria in substantially aqueous sample.

Figure 2:
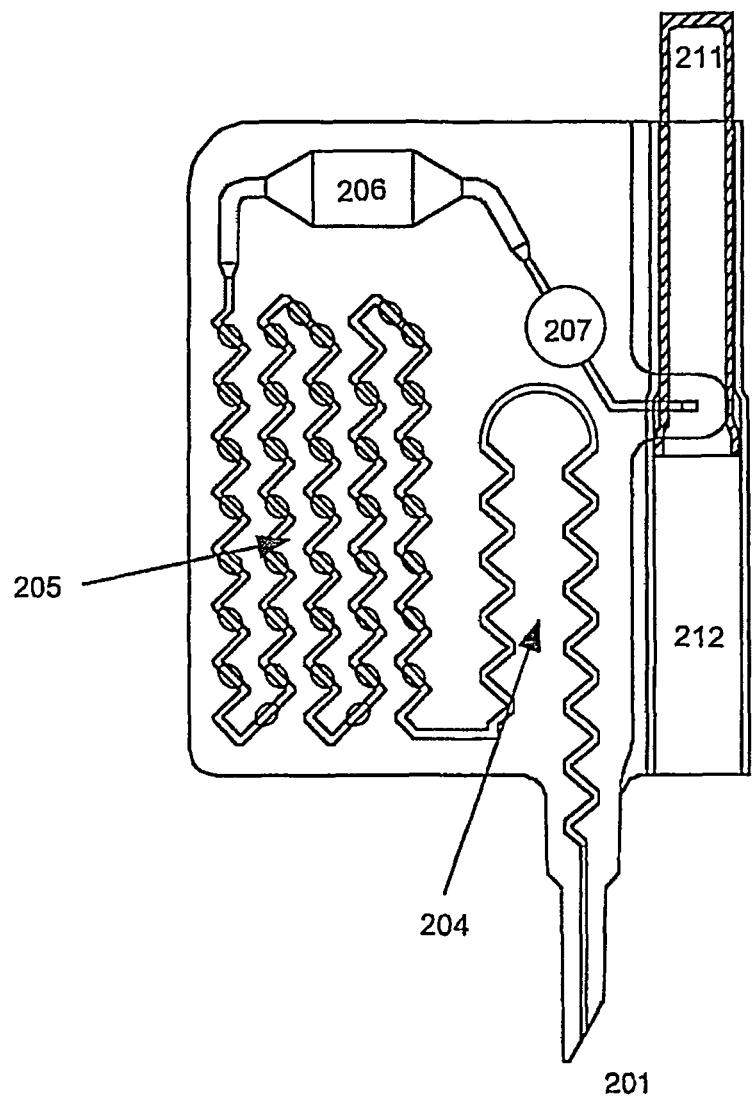
FIG. 2 illustrates a disposable device used for the assessment of the number of somatic cells in milk.

Turning now to FIG. 2 which illustrates a possible arrangement of flow components in a disposable device which could be suited for the assessment of somatic cells in milk, preferably the counting of the number of somatic cells in a volume of milk.

The disposable device which is drawn in FIG. 2 consists of an inlet 201 which has the form of a tip which is immersed in the sample being measured prior to loading of a part of the sample into the disposable device. It further consists of a reaction component chamber 204 where any reaction component is placed prior to analysis. The sample loaded into the device preferably remains in the chamber 204 for a time sufficient to dissolve or disperse the reaction component(s). This relates in particular to the situation wherein the components are on solid form. Connected to the reaction component chamber is a channel 203 which consists substantially of narrow flow channels with diameter of around 0.5 mm which has shape which causes any liquid flowing in the channel to change the direction of flow for a number of time by introducing several bends in the flow channel, as well as a number of relatively small mixing chamber which is placed between the bends. The exposure of signals from the sample is performed in the sample compartment 204 which is formed by two substantially parallel walls with space of about 80 µm defining the depth of the flow sample compartment. Any liquid passing through the sample compartment flows toward a valve 205 which is a block of substantially porous material which is treated with matter which expands upon contact with liquid, thus allowing gas to pass, but substantially closing any flow upon contact with liquid. This material is provided by Porex Technologies GmbH, Germany (XM-1378, EDP#NS-7002). The disposable device also contains a piston 206 positioned in a piston cylinder 207, the piston and the cylinder being arranged in such a way that a substantially reduced pressure is formed when the piston is pressed into the cylinder. The valve, and consequently the remaining components of the flow system are connected to the piston cylinder, in such a way that the reduced pressure can propel the sample through the inlet, and further towards the valve.

While the tip is immersed in the sample the piston is pressed partly into the piston cylinder. This reduced pressure formed causes the sample to enter the inlet and into a reaction component chamber which has previously been loaded with approximately 2 to 8 µl of an aqueous solution containing Propidlum Iodide (0.12% w/w), Triton X-100 (7% w/w) and Ammonium Chloride (14% w/w) and after loading the aqueous solution is dried to dryness in hot air resulting in a substantially non-aqueous reaction component.

The movement of the piston allows a substantially determined volume of the milk to enter the inlet, the volume of the sample being at least substantially equal to the volume of the flow system between the valve and extending beyond the sample compartment, so that when the liquid is in contact with the valve, then the sample compartment should be at least partly, and preferably completely filled. The device illustrated in this example makes it suitable to take a volume of preferably about 40 µl.

When the inlet has been removed from the sample, then the piston is pressed further into the cylinder, thus causing the sample to flow into the valve, causing it to dose. This second activation of the piston is preferably carried out in connection with the engagement of the sample device in a system, containing at least a detection device capable of detecting the signal from the sample compartment, preferably the detection of fluorescence from Propidium Iodide at above 575 nm when exited with light of about below 550 nm.

The body of the disposable device is made from a polymer material, preferably such material which allows the exposure of fluorescence signals, thus allowing the walls of the sample compartment to be an integral part of the body of the device.

The device is preferably assembled by having at least two parts of polymer material which make up the body of the device, where the different parts of the flow system are engraved in at least one of the parts. When reaction components have been loaded into me reaction component chamber, and the valve material has been placed in the valve compartment then the two parts are assembled, either by ultrasonic welding or by the use of adhesive materials.

For the protection of the windows and/or to improve the stability of the chemicals in the reaction component compartment, it is often preferred to enclose the device into a substantially closed container, e.g. a container of thin film assembled to form a bag.

Figure 3:
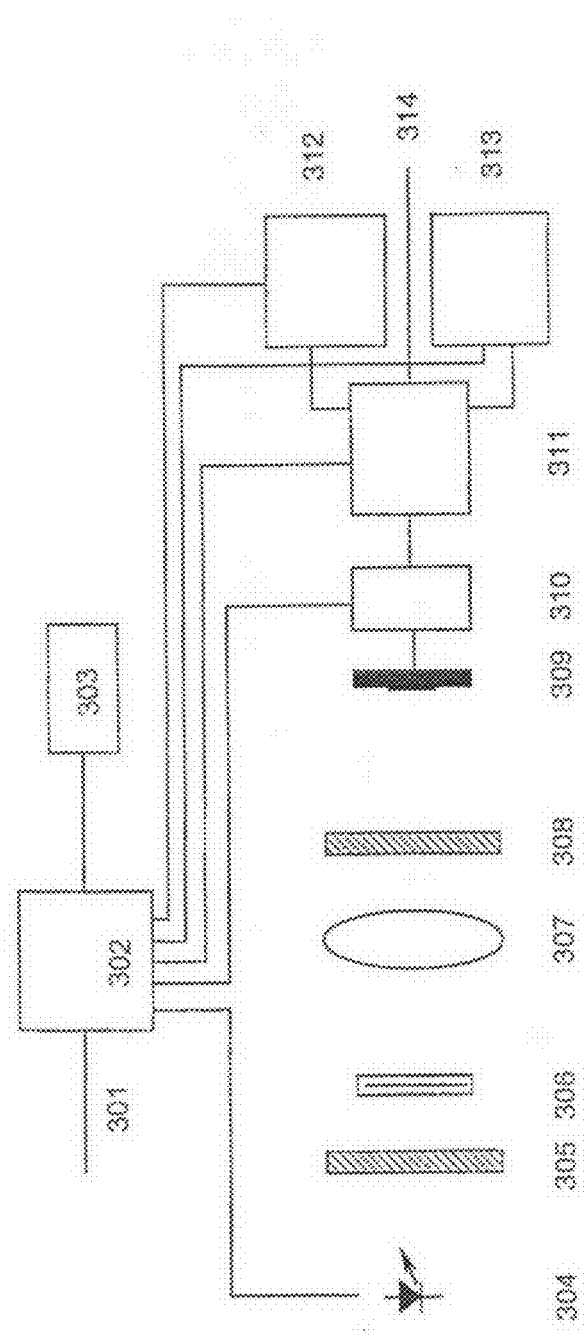
FIG. 3 illustrates a system for the assessment of the number of somatic cells in milk using a disposable device.

FIG. 3 illustrates an instrument or a system which can be used for the assessment of the number of somatic cells in a volume of milk sample. The instrument is powered by either an external power source 301 or by an internal power source such as a lead acid (12V 2.2Ah) rechargeable battery 303, manufactured by Wetronic Inc. (WE12-2.2).

Figure 6:
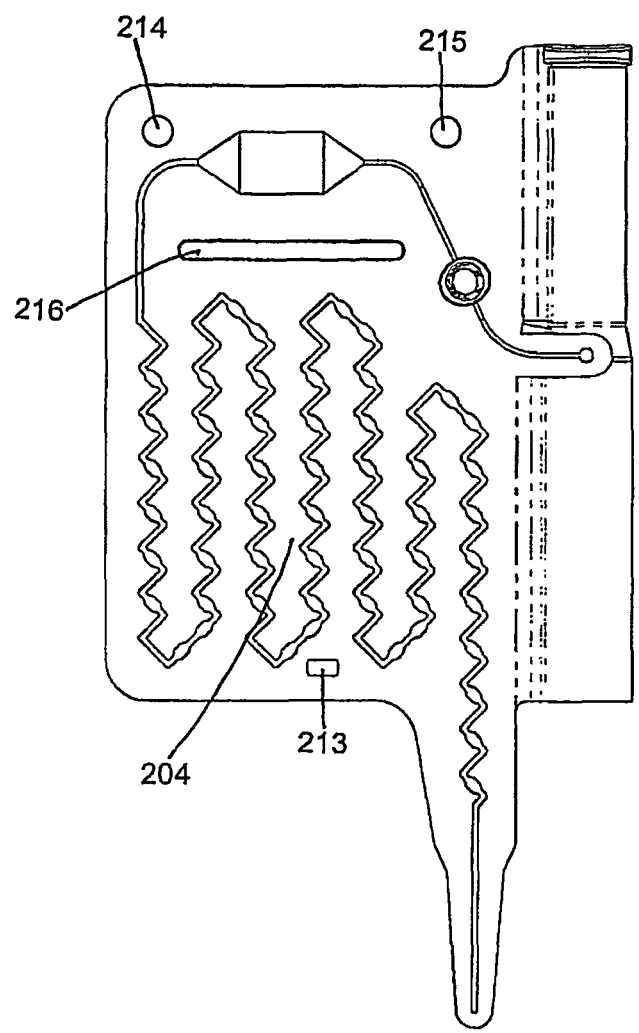
FIG. 6 illustrates another embodiment of a disposable device used for the assessment of the number of somatic cells in milk.

In FIG. 6 another embodiment of the device is shown. In particular, the reaction component chamber 204 is formed with regularly arranged extensions whereby a premixing of the sample and reagent is provided. Also the device of FIG. 6 is provided with recesses 213, 214, 215 and 216 which can be used when arranging the device correctly in the detection device of the system and/or for the orientation of the device during production.

The Power supply/battery charger 302 supplies the different units of the instrument. The power supply can use power from either the external or the internal power source, and is capable of switching between the two sources during operation. It is possible to reduce the power consumption when the instrument is in stand-by.

The assessment of the number of somatic cells is performed by detecting a fluorescence signal originating from a fluorochrome bounded to DNA within somatic cells present in the sample compartment 306 which is a part of a disposable device, preferably a disposable device similar to the one described in Example 2. The sample compartment is defined by two substantially parallel planes of transmitting material thus forming a compartment with dimensions of about 10×10×0.08 mm (height, width, depth).

The fluorescence is generated by passing light of high energy (excitation light of wavelength 550 nm or less) through the sample compartment, with direction towards the detection module 311. The source 304 of the excitation light can be a number of light emitting diodes, for instance 4 or more, of type NSPG-500S or NSPE-590S (Nichia Chemical Industries Ltd., Japan).

In order to remove substantially any component from the excitation light with wavelength above 550 nm from reaching the sample compartment, an optical filter 305 is inserted in the light path. This filter of the type Ferroperm SWP550, double sided interference filter on a 2 mm substrate (Hoya, CM-500) which absorbs infra-red radiation.

The light emitted from the sample compartment is focused onto the sensors of the detection module by the use of at least one lens 307. This lens is a standard ×4 microscope objective with numerical aperture of 0.10 (Supplied by G. J. Carl Hansens Eftf., Denmark). The lens is arranged in such a way as to give an image of an object in the sample compartment on the sensors of the detection module which has approximately the same size as the original object (magnification approximately ×1).

In order to remove substantially any component from the light emitting from the sample compartment with wavelength below 575 nm from reaching the detection module, an optical filter 308 is inserted in the light path. This filter is of the type Schott OG590(thickness 3 mm).

The filtered light from the sample compartment is detected by a charge couple device (CCD) 309 of the type GCA325KBL (supplied by L&G Semicon). The CCD is equipped with 510×492 detection elements.

The electrical information from the CCD is amplified and measured by an analogue to digital converter module 310 (ADC).

The operation of the instrument is controlled by the computer unit 311. The computer is a Motorola DSP56824 16 bit digital signal processor, equipped with non-volatile storage capacity for long time storage (EEPROM) as well as volatile storage capacity (RAM). The computer gathers information about the measured light intensity of each detection element of the CCD from the ADC module and uses it for the assessment of the number of somatic cells in the milk sample present in the sample compartment The computer module is equipped with a real time dock.

The result of the assessment of the number of somatic cells in the milk sample is presented on a display 313 of type MDLS16166-3V (supplied by Varitronix).

The result of the assessment of the number of somatic cells in the milk sample can also be transmitted to an external computer (not shown) by the use of the output port 314.

The user of the instrument can control its operation, and enter relevant information through a collection of keys forming a key-pad 312. The key-pad is a 16 keys module of type ECO 16250 06 SP.

EXAMPLES

Example 1

Principle for Assessment of Bacteria by Substantially Specific Binding to Paramagnetic Beads It is often of interest to assess a specific bacteria, where the purpose of the assessment is to determine the possible presence of the bacteria in a sample. One such assessment is the assessment of *Salmonella* bacteria, where the sample material can be a sample derived from food, or a sample from an enrichment culture.

This can be done, by preparing a number of paramagnetic beads which have been treated with a *Salmonella* specific antibody, preferably covalently linked to the surface of the bead. The beads can be placed in a compartment of the disposable device prior to analysis, or they can be added to the sample material being sampled. The reaction between the *Salmonella* bacteria and the *Salmonella* specific antibody on the surface of the beads which binds the bacteria to the bead is normally completed in a relatively short period of time (normally few minutes or less), and can take place in a reaction chamber of the disposable device, or in an external vessel.

When the reaction between *Salmonella* bacteria and the beads is substantially completed the sample can be propelled into or through the sample compartment, where signals from the *Salmonella* bacteria, or any molecules bound to or interacting with the *Salmonella* bacteria (e.g. fluorescence signals from specific or non-specific dye molecules) is emitted to the exterior. If the sample compartment is exposed to the force of a magnetic field while the sample is propelled through the sample compartment (particle retaining means) then at least a part of the beads, and thus at least a part of any *Salmonella* bacteria bound to a bead, which are present in the sample are retained in the sample compartment, thus allowing substantially large volumes being analysed in one or few exposures.

If any further interaction between the beads, and/or the *Salmonella* bacteria bound to the beads, and any reaction component is needed (e.g. washing bacteria not bound to beads, reaction with a dye, etc.), this interaction can often take place within the sample compartment, preferably while the beads are exposed to a magnetic force field.

The disposable device can be equipped with compartments capable of retaining any sample entering the device, as well as any reaction component added, and thus supplying means for safe handling of any *salmonella* containing waste.

Depending on the nature of the detection device, it can be of interest to be able to adjust the focusing of any focusing mean used by the detection mean, in such a way as to improve the quality of the assessment.

Example 2

Principle for the Assessment of Bacteria in Water Retained on a Filter Device.

A disposable device, similar to the one described in relation to FIG. 2, with a modification where filter means, capable of substantially retaining any bacteria passing the filter means, are placed in the sample compartment 204 and arranged in such a way that signals from particles retained on the filter means are exposed to the exterior, and where suitable reservoir is placed between the sample compartment and the valve 205 with volume capable of holding the volume of sample passed through the filter.

The filter means could be a filter capable of retaining the bacteria to be assessed, for instance it could be a filter with an average pour size of 0.22 μm. The filter is placed in the sample compartment, arranged substantially parallel to a window of the sample compartment allowing signals from particles retained on the filter means to pass to the exterior and be detected by detection means, preferably in instrument similar to the one described in relation to FIG. 3. The instrument should preferably contain focusing means capable of adapting the focusing to the conditions given by the individual disposable device. The excitation means comprising at least a source 304 and an optical filter 305 should preferably be placed on the same side of the sample compartment as the detection device, if the properties of the filter means or other properties of the sample compartment do substantially not allow the electromagnetic excitation irradiation to pass through.

The disposable device is loaded with aqueous mixture of reaction components comprising Propidium Iodide (0.12% w/w) Triton X-100 (7% w/w), Ammonium Chloride (14% w/w) and EDTA (1% w/w) in amount corresponding to the volume of sample which is to be analysed, giving a predetermined concentration of the reaction components in the sample. The aqueous mixture is dried in hot air giving reaction components on substantially dry non-aqueous form, contained in the reaction chamber 204. The reaction components react with the bacteria in a way which allows Propidium Iodide to bind to DNA molecules within the bacteria The Propidium iodide molecules give rise to fluorescence at above 570 nm when excited with electromagnetic irradiation of below 550 nm.

A volume of the sample to be analysed is sampled by immersing the inlet 201 in the sample and moving the piston 206 into the piston cylinder 207 thus causing a reduction of pressure in the flow system capable of propelling the sample from the inlet towards the valve 205 and thus allowing an approximately known volume of the sample to pass through the filter means, the size of the volume passing the filter means being determined depending on the nature of the assessment, a volume of between 10 μl and 1000 μl often being adequate, but in some embodiments volumes larger than 1000 μl could be used. The sample dissolves the reaction components and the sample and the reagent components are at least partially mixed in the mixing part 203 of the disposable device. The volume of the reagent chamber and the mixing part are adapted to the volume of the sample to be analysed.

Example 3

The Assessment of the Number of Somatic Cells in a Volume of Milk According to the Present Invention.

104 raw milk samples from individual cows were collected and measured on a FossoMatic (Foss Electric, Denmark) in order to obtain an estimate of a reference value for the number of somatic cells in volume of milk. For comparison portions of the same samples were measured in a device according to the present invention as described in relation to FIG. 2.

The sample compartment of the devices used for the analysis was on average about 67 μm in thickness, with a variation of about 1 μm expressed as one standard deviation of the measured thickness. The effect of varying thickness of the sample compartment was not compensated for in the results.

Prior to analysis the reaction compartment of the device was loaded with approximately 6 μl solution containing Propidium Iodide (0.06% w/w), Triton X-100 (3.5% w/w) and Ammonium Chloride (7% w/w). The solution was dried in hot air resulting in substantially removal of water. The substantially dried reaction components where at least partially dissolved by passing approximately 50 μl of milk sample to the reaction compartment.

Figure 4:
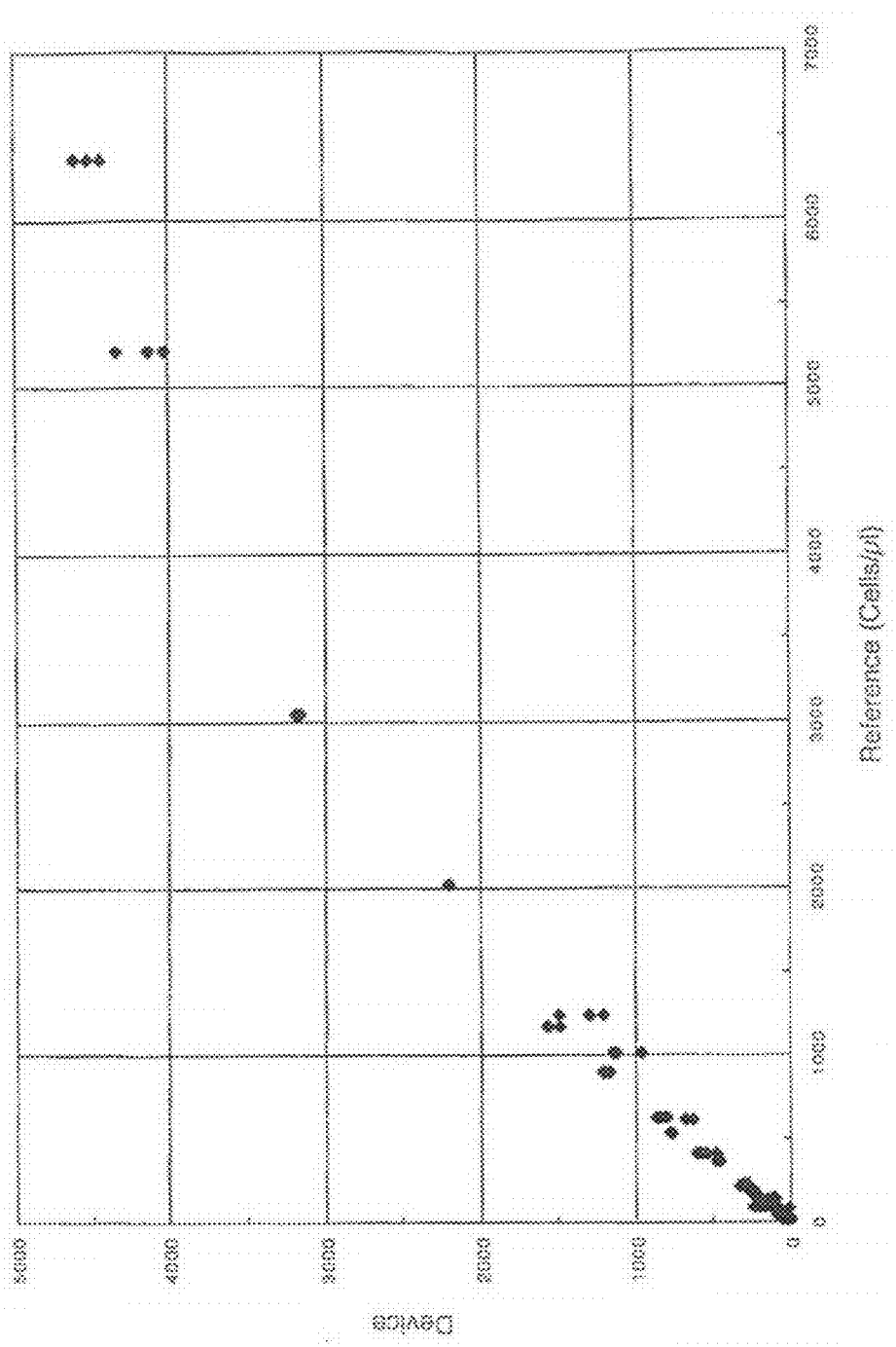
FIG. 4 illustrates a graph where results of the counting of somatic cells in milk according to the present invention are plotted against reference values.

The results of these measurements are given in FIG. 4 which shows a graph of the results obtained according to the method of the present invention versus the reference values.

As can be seen from FIG. 4 then there is a clear correlation between the results obtained according to the present invention and the reference values. The deviation from linear relationship between the two methods which is apparent for samples with more than about 3000 cells/μl is possibly caused by the increased probability of two or more cells occupying substantially the same area of the sample compartment when it is viewed as an image.

Example 4

The Assessment of the Number of White Blood Cells in a Sample of Human Whole Blood According to the Present Invention.

9 samples of human whole blood were measured on a standard routine cell counter (unknown fabricate) in order to obtain an estimate of a reference value for the number of white blood cells in volume of human blood. For comparison portions of the same samples were measured in a device according to the present invention as described in relation to FIG. 2. Each sample was measured twice in two separate devices.

The sample compartment of the devices used for the analysis was on average about 41 μm in thickness, with a variation of about 0.7 μm expressed as one standard deviation of the measured thickness. The effect of varying thickness of the sample compartment was compensated for in the results.

Prior to analysis the reaction compartment of the device was loaded with approximately 6 μl solution containing Propidium Iodide (0.03% w/w), Triton X-100 (1.7% w/w) and Ammonium Chloride (3.5% w/w). The solution was dried in hot air resulting in substantially removal of water. The substantially dried reaction components where at least partially dissolved by passing approximately 30 μl of whole blood sample to the reaction compartment.

Figure 5:
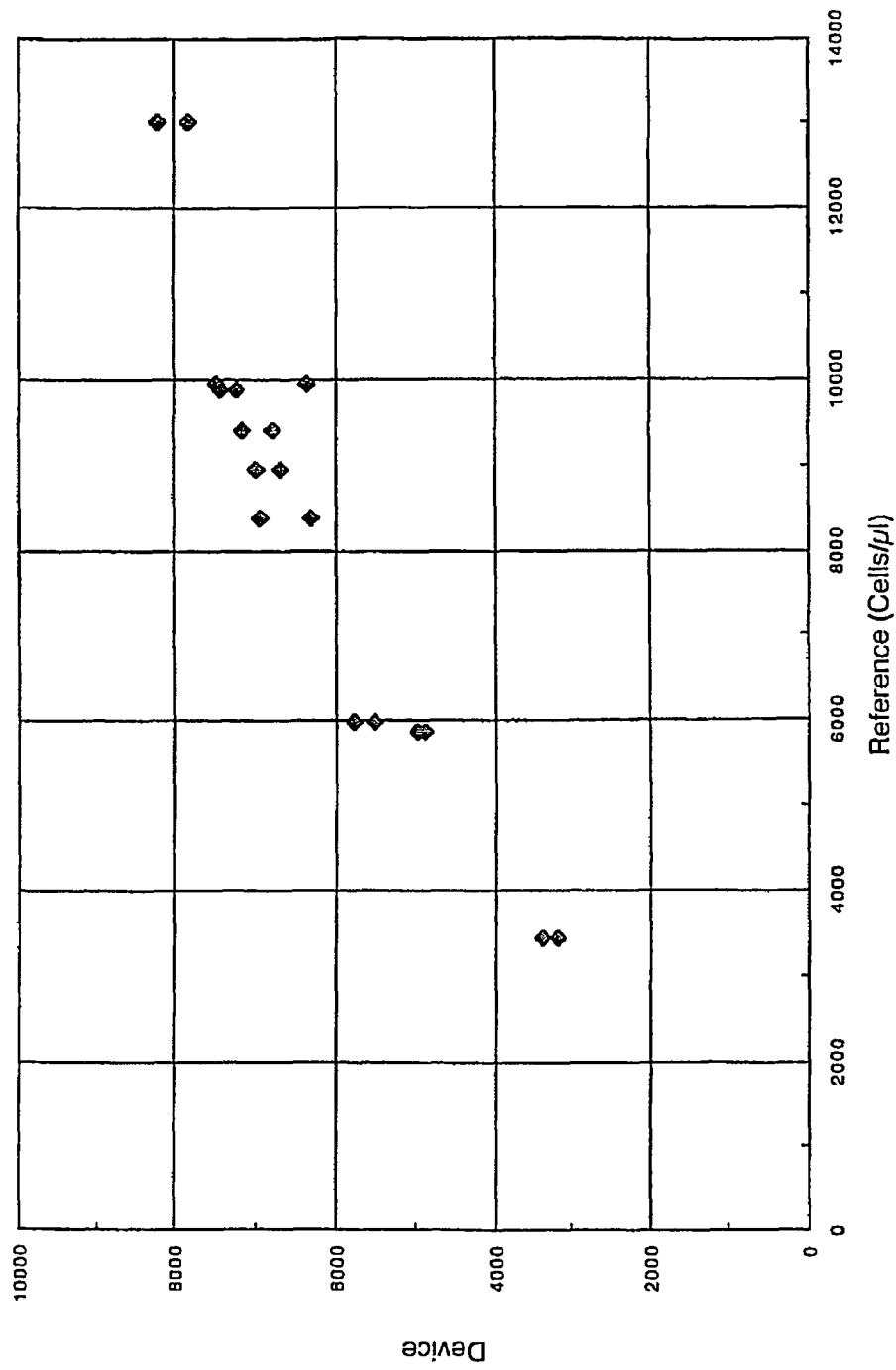
FIG. 5 Illustrates a graph where results of the counting of somatic cells in blood according to the present invention are plotted against reference values.

The results of these measurements are given in FIG. 5 which shows a graph of the results obtained according to the method of the present invention versus the reference values.

As can be seen from FIG. 5 then there is a clear correlation between the results obtained according to the present invention and the reference values.

The invention claimed is:

1. A sampling device adapted to be used in a system for the assessment of the number of particles in a liquid analyte material, the sampling device comprising
   a sample compartment including an exposing domain, said exposing domain allowing electromagnetic signals from a sample in the exposing domain to pass to a detection device so as to form spatial image of the exposing domain on the detection device,
   only one inlet through which a volume of a liquid sample representing the analyte material can be introduced, and having no sample outlet,
   a flow system having at least a channel allowing at least a portion of the volume of the liquid sample to flow within the sampling device, wherein at least a part of the channel through which the sample flows before entering the sample compartment has a plurality of bends or obstructions resulting in substantial turbulent flow in liquid passing the bends or obstructions, and
   said sampling device being configured to position said exposing domain in relation to said detection device to provide an assessment of said at least one particle parameter of the liquid analyte material,
   the device having data concerning dimensions of the device which influence the volume of the exposing domain, the data being readable by the detection device or another device adapted to read the data.

2. A sampling device according to claim 1, wherein the flow system additionally comprises a compartment or a flow channel part in which at least a part of one or more reaction components initially loaded in the compartment or flow channel is added to at least a portion of the volume of the liquid sample representing the analyte material.

3. A sampling device according to claim 2, wherein at least one of the reaction components is in freeze-dried form.

4. A device according to claim 1, wherein part of the channel provides laminar flow in the liquid sample.

5. A sampling device according to claim 1, wherein the flow system has one or more means for regulating the velocity of the flow into or within the device.

6. A sampling device according to claim 1, wherein the sampling device has a filter material and can perform one or more operations on the liquid sample, the operations being selected from the group consisting of filtration, concentration and magnetic attraction.

7. A sampling device according to claim 1, containing one or more compartment(s) or domain(s) which allows spectrophotometric measurement for the determination of any chemical property, the spectrophotometric measurement being selected from the group consisting of: mid-infrared attenuation, near- infrared attenuation, visible attenuation, ultra-violet attenuation, photoluminescence, raman scatter, and nuclear magnetic resonance.

8. A sampling device according to claim 1, wherein the interior of the sample compartment has an average depth of between 20 μm and 2000 μm.

9. A sampling device according to claim 1, wherein the sample compartment has dimensions, in a plane parallel to an exposing window, in the range between 1 mm by 1 mm and 10 mm by 10 mm.

10. A sampling device according to claim 1, wherein the volume of the exposing domain is in the range between 0.01 μl and 20 μl.

11. A sampling device according to claim 1, wherein the flow system comprises one or more mixing chambers.

12. A sampling device according to claim 1, wherein the interior of the sample compartment has an average depth of between 20 μm and 1000 μm.

13. A sampling device according to claim 1, wherein the interior of the sample compartment has an average depth of between 20 μm and 200 μm.

14. A sampling device according to claim 1, wherein the volume of exposing domain is in the range between 0.04 μl and 4 μl.

15. A sampling device according to claim 1, wherein the sampling device includes a propelling element.

16. A sampling device according to claim 1, wherein the sampling device is configured to form, in the detection device, a processable spatial image representation of the at least one particle parameter in said exposing domain.

17. A sampling device according to claim 1, wherein the sampling device is a single use device for assessing only one volume of said liquid sample introduced through said one inlet.

18. A sampling device according to claim 1, wherein the sampling device is disposable.

* * * * *